United States Patent
Park et al.

(10) Patent No.: US 9,394,562 B2
(45) Date of Patent: Jul. 19, 2016

(54) SOIL MICROORGANISM, NOVEL OXIDOREDUCTASE SEPARATED FROM THE SOIL MICROORGANISM, GENE ENCODING THE OXIDOREDUCTASE, AND METHOD FOR PRODUCING AGLYCONES USING THE MICROORGANISM, THE OXIDOREDUCTASE AND THE GENE

(71) Applicants: AMOREPACIFIC CORPORATION, Seoul (KR); SNU R&DB Foundation, Seoul (KR)

(72) Inventors: Jun Seong Park, Suwon-si (KR); Duck Hee Kim, Seoul (KR); Han Kon Kim, Suwon-si (KR); Eun Mi Kim, Seoul (KR); Byung Gee Kim, Seoul (KR)

(73) Assignees: AMOREPACIFIC CORPORATION (KR); SNU R&DB FOUNDATION (KR)

( * ) Notice: Subject to any disclaimer, the term of this patent is extended or adjusted under 35 U.S.C. 154(b) by 16 days.

(21) Appl. No.: 14/588,790

(22) Filed: Jan. 2, 2015

(65) Prior Publication Data
US 2015/0184216 A1 Jul. 2, 2015

Related U.S. Application Data

(63) Continuation of application No. 13/704,210, filed as application No. PCT/KR2011/004361 on Jun. 14, 2011, now abandoned.

(30) Foreign Application Priority Data

Jun. 14, 2010 (KR) .......................... 10-2010-0055988
Jul. 9, 2010 (KR) .......................... 10-2010-0066307

(51) Int. Cl.
| | | |
|---|---|---|
| C12Q 1/26 | (2006.01) | |
| C12P 33/20 | (2006.01) | |
| C12N 9/02 | (2006.01) | |
| C12P 17/06 | (2006.01) | |
| C12P 19/02 | (2006.01) | |
| C12P 33/00 | (2006.01) | |
| C12R 1/41 | (2006.01) | |
| C12N 1/20 | (2006.01) | |

(52) U.S. Cl.
CPC . *C12P 33/20* (2013.01); *C12N 1/20* (2013.01); *C12N 9/0004* (2013.01); *C12P 17/06* (2013.01); *C12P 19/02* (2013.01); *C12P 33/00* (2013.01); *C12R 1/41* (2013.01); *Y02P 20/52* (2015.11)

(58) Field of Classification Search
CPC .................................................. C12Y 101/00
USPC ........................................... 435/25, 189, 200
See application file for complete search history.

(56) References Cited

U.S. PATENT DOCUMENTS

| 2004/0028671 A1 | 2/2004 | Jin et al. |
| 2011/0091944 A1 | 4/2011 | Wu et al. |
| 2012/0309918 A1 | 12/2012 | Ruijssenaars et al. |

FOREIGN PATENT DOCUMENTS

| CN | 1232875 A | 10/1999 |
| EP | 0950715 A2 | 10/1999 |
| JP | 2002017372 | 1/2002 |
| KR | 1020000062140 A | 10/2000 |
| KR | 100945586 B1 | 2/2010 |
| KR | 100945587 B1 | 2/2010 |

OTHER PUBLICATIONS

Glucoside 3-dehydrogenase (EC 1-1.99.13)—*Halomonas* sp. alpha-15, Feb. 8, 2012, Retrieved from the internet:, URL:http://www.ncbi.nlm.nih.gov/protein/25392214?report=genbank&log$=prottop&blast.
International Search Report—PCT/KR2011/004361 dated Mar. 16, 2012.
Oxidoreductase [Agrobacterium tumefaciens str. C58], Feb. 8, 2012, Retrieved from the internet:,URL:http://www.ncbi.nlm.nih.gov/protein/15890606?sat=13&satkey=10200034.
Oxidoreductase [Sphingobacterium spiritivorum ATCC 33300], Feb. 9, 2012, Retrieved from the internet:,URL:http://www.ncbi.nlm.nih.gov/protein/227540026?sat=11&satkey=1715970.
Putative Oxidoreductase [Stenotrophomonas maltophilia K279a], Feb. 9, 2012, Retrieved from the internet:,URL:http://www.ncbi.nlm.nih.gov/protein/190573214?sat=13&satkey=10359214.
Written Opinion—PCT/KR2011/004361 dated Mar. 16, 2012.
Japanese Office Action—Japan Application No. JP2013-515263 issued on May 26, 2015.

*Primary Examiner* — Tekchand Saidha
(74) *Attorney, Agent, or Firm* — Cantor Colburn LLP

(57) ABSTRACT

The present invention relates to the novel *Rhizobium* sp. GIN611 KCTC11708BP or to cell extracts thereof, to a novel oxidoreductase which exhibits a glycolytic activity, to a gene encoding the oxidoreductase, to a recombinant strain comprising recombinant vector proteins or to an expression vector encoding recombinant proteins, and to a method for the glycolysis of natural products using same as a biocatalyst. The present invention also relates to a method for producing aglycones from a variety of natural products using same. The novel oxidoreductase separated from the novel microorganism of the present invention does not belong to a glucosidase group but belongs to an oxidoreductase group, and has a glycolytic activity for natural products. The novel oxidoreductase oxidizes the sugar in the aglycones of natural products, thereby producing a variety of aglycones.

3 Claims, 12 Drawing Sheets

| Ginsenosides | $R_1$ | $R_2$ |
|---|---|---|
| Rb1 | -Glc(2→1)Glc | -Glc(6→1)Glc |
| Rb2 | -Glc(2→1)Glc | -Glc(6→1)Arap |
| Rb3 | -Glc(2→1)Glc | -Glc(6→1)Xyl |
| Rc | -Glc(2→1)Glc | -Glc(6→1)Araf |
| Rd | -Glc(2→1)Glc | -Glc |
| Rg3 | -Glc(2→1)Glc | -H |
| F2 | -Glc | -Glc |
| Rh2 | -Glc | -H |
| CK | -H | -Glc |
| Compound Y | -H | -Glc(6→1)Arap |
| Mc | -H | -Glc(6→1)Araf |
| Mx | -H | -Glc(6→1)Xyl |
| PPD(S) | -H | 2D(S)-H |

Glc: β-D-glucopyranosyl
Arap: α-L-arabinopyranosyl
Araf: α-L-arabinofuranosyl
Xyl: β-D-xylopyranosyl

| Ginsenosides | $R_1$ | $R_2$ |
|---|---|---|
| Re | -Glc(2→1)Rha | -Glc |
| R1 | -Glc(2→1)Glc | -H |
| Rg2 | -Glc(2→1)Rha | -H |
| R1 | -Glc(2→1)Xyl | -Glc |
| Rg1 | -Glc | -Glc |
| F3 | -H | -Glc(6→1)Arap |
| Rh1 | -Glc | -H |
| F1 | -H | -Glc |
| PPT(S) | -H | -H |

Glc: β-D-glucopyranosyl
Arap: α-L-arabinopyranosyl
Rha: α-L-rhamnopyranosyl
Xyl: β-D-xylopyranosyl M: size marker
LB: complete medium
    (60-80 % saturated ammonium sulfate fraction)
RG: M9/ginsenoside medium
    (60-80% saturated ammonium sulfate fraction)

Fig.8

GAATGCGAGCTTACCATGCAGTCGAGCGCCCCGCAAGGGGAGCGGCAGACGG
GTGAGTAACGCGTGGGAATCTACCGAGCCCTGCGGAATAGCTCCGGGAAACT
GGAATTAATACCGCATACGCCCTACGGGGGAAAGATTTATCGGGGTTTGAT
GAGCCCGCGTTGGATTAGCTAGTTGGTGGGGTAAAGGCCTACCAAGGCGACG
ATCCATAGCTGGTCTGAGAGGATGATCAGCCACATTGGGACTGAGACACGG
CCCAAACTCCTACGGGAGGCAGCAGTGGGGAATATTGGACAATGGGCGCAAG
CCTGATCCAGCCATGCCGCGTGAGTGATGAAGGCCCTAGGGTTGTAAAGCTC
TTTCAACGGTGAAGATAATGACGGTAACCGTAGAAGAAGCCCCGGCTAACT
TCGTGCCAGCAGCCGCGGTAATACGAAGGGGGCTAGCGTTGTTCGGAATTAC
TGGGCGTAAAGCGCACGTAGGCGGATATTTAAGTCAGGGGTGAAATCCCGG
GGCTCAACCTCGGAACTGCCTTTGATACTGGGTATCTTGAGTATGGAAGAG
GTAAGTGGAATTGCGAGTGTAGAGGTGAAATTCGTAGATATTCGCAGGAAC
ACCAGTGGCGAAGGCGGCTTACTGGTCCATTACTGACGCTGAGGTGCGAAAG
CGTGGGGAGCAAACAGGATTAGATACCCTGGTAGTCCACGCCGTAAACGAT
GAATGTTAGCCGTCGGGCAGTATACTGTTCGGTGGCGCAGCTAACGCATTA
AACATTCCGCCTGGGGAGTACGGTCGCAAGATTAAAACTCAAAGGAATTGA
CGGGGCCCGCACAAGCGGTGGAGCATGTGGTTTAATTCGAAGCAACGCGCA
GAACCTTACCAGCTCTTGACATTCGGGGTATGGGCAGTGGAGACATTGTCC
TTCAGTTAGGCTGGCCCAGAACAGGTGCTGCATGGCTGTCGTCA

SEQUENCE LISTING

<160> NUMBER OF SEQ ID NOS: 3

<210> SEQ ID NO 1
<211> LENGTH: 971
<212> TYPE: DNA
<213> ORGANISM: Rhizobium sp. GIN611

<400> SEQUENCE: 1

```
gaatgcgagc ttaccatgca gtcgagcgcc ccgcaagggg agcggcagac gggtgagtaa      60
cgcgtgggaa tctaccgagc cctgcggaat agctccggga aactggaatt aataccgcat     120
acgccctacg ggggaaagat ttatcggggt ttgatgagcc cgcgttggat tagctagttg     180
gtggggtaaa ggcctaccaa ggcgacgatc catagctggt ctgagaggat gatcagccac     240
attgggactg agacacggcc caaactccta cgggaggcag cagtggggaa tattggacaa     300
tgggcgcaag cctgatccag ccatgccgcg tgagtgatga aggccctagg gttgtaaagc     360
tctttcaacg gtgaagataa tgacggtaac cgtagaagaa gccccggcta acttcgtgcc     420
agcagccgcg gtaatacgaa gggggctagc gttgttcgga attactgggc gtaaagcgca     480
cgtaggcgga tatttaagtc aggggtgaaa tcccggggct caacctcgga actgcctttg     540
atactgggta tcttgagtat ggaagaggta agtggaattg cgagtgtaga ggtgaaattc     600
gtagatattc gcaggaacac cagtggcgaa ggcggcttac tggtccatta ctgacgctga     660
ggtgcgaaag cgtggggagc aaacaggatt agataccctg gtagtccacg ccgtaaacga     720
tgaatgttag ccgtcgggca gtatactgtt cggtggcgca gctaacgcat taaacattcc     780
gcctgggagt tacggtcgca agattaaaac tcaaaggaat tgacggggcc cgcacaagc      840
ggtggagcat gtggtttaat tcgaagcaac gcgcagaacc ttaccagctc ttgacattcg     900
gggtatgggc agtggagaca ttgtccttca gttaggctgg ccccagaaca ggtgctgcat     960
ggctgtcgtc a                                                           971
```

<210> SEQ ID NO 2
<211> LENGTH: 1686
<212> TYPE: DNA
<213> ORGANISM: Rhizobium sp. GIN611

<400> SEQUENCE: 2

```
atggcgaata atcattacga cgcgattgtt gtcggttcgg ggatcagcgg aggctgggcc      60
gcaaaagaac tcacacaaaa gggtctaaaa gttcttcttc ttgaacgtgg cagaaacatt     120
gaacacatca ccgattacca gaatgcagac aaggaagcgt gggactaccc tcaccgcaat     180
cgtgccacgc aggaaatgaa ggcaaagtat ccggttctga gccgcgatta tctgttggaa     240
gaagccacac tcggcatgtg ggctgacgaa caagaaacgc cttacgtcga agaaaaacgt     300
```

```
ttcgattggt tccgtgggta ccacgtgggt ggtcgttctc tcctttgggg ccgtcaaacc    360
tatcgatggt cacagaccga ttttgaggcc aatgcaaaag aaggcatcgc tgttgattgg    420
cctattcgtt accaggatgt tgcgccgtgg tacgactacg ttgaacggtt tgcgggcatt    480
tccggcagca aagaagggct cgatatcctt cctgatggtg aattccttcc accaatccct    540
ttgaactgcg tagaagaaga tgtggcgcgt cgtctgaagg acaggttcaa gggcacgcgt    600
cacctgatca attcccgctg cgccaacatc acacaggaac ttcctgacca ggatcgcaca    660
cgctgtcagt tcagaaacaa gtgtcggttg ggctgtccgt tcggcggtta cttcagcaca    720
caatcatcaa ccctgcctgc ggccgtcgcg accggcaatc tcaccctgcg ccgttctca    780
atcgtcaagg agatccttta cgacaaggac aagaagaagg cccgcggtgt cgagatcatc    840
gatgccgaaa ccaacatgac ctatgaatat accgcagaca ttatcttcct gaatgcctca    900
acgctgaatt cgacctgggt cctgatgaac tcagccaccg acgtgtggga agggggattg    960
ggaagcagtt ccggcgaact cggccacaat gtcatggacc atcatttccg catgggtgcg   1020
acgggtgagg tcgaaggatt tgacgagttc tatttcaagg acgccgcccg gcaggtttc   1080
tacattcctc gcttccgcaa catcggcgat gaaaagcgta atatctgcg tggttttggt   1140
tatcagggtt cggcaagccg ctcccgctgg gagcgcgaaa tcgccgagat gaatattgga   1200
gcagattata aagacgcgtt gaccgaacca ggcggctgga caatcggcat gacagccttt   1260
ggcgagatgc tgccctacca cgaaaatcgc gtgaagcttg accaaaacaa aaaggacaaa   1320
tgggggttgc cggtccttc aatgaatgtc gagttgaaac aaaacgaact cgatatgcgt   1380
gaagacatgg tgaatgacgc tgtcgaaatg ttgaggccg tcggcatcaa gaacgtcaaa   1440
ccgacccgag gcagctacgc acccggtatg ggtattcacg aaatgggaac ggcgcgcatg   1500
ggccgcgatc caaagtcttc ggttctaaat ggcaacaacc aggtgtggga tgcccctaac   1560
gtgttcgtga cggatggtgc ctgcatgacg tctgctgcct gtgtaaatcc gtctctcacc   1620
tacatggcac tgacggcacg tgccgccgat tttgccgtgt cagagctcaa gaagggaaat   1680
ctgtaa                                                              1686
```

<210> SEQ ID NO 3
<211> LENGTH: 561
<212> TYPE: PRT
<213> ORGANISM: Rhizobium sp. GIN611

<400> SEQUENCE: 3

```
Met Ala Asn Asn His Tyr Asp Ala Ile Val Val Gly Ser Gly Ile Ser
  1               5                  10                  15

Gly Gly Trp Ala Ala Lys Glu Leu Thr Gln Lys Gly Leu Lys Val Leu
             20                  25                  30

Leu Leu Glu Arg Gly Arg Asn Ile Glu His Ile Thr Asp Tyr Gln Asn
         35                  40                  45

Ala Asp Lys Glu Ala Trp Asp Tyr Pro His Arg Asn Arg Ala Thr Gln
     50                  55                  60

Glu Met Lys Ala Lys Tyr Pro Val Leu Ser Arg Asp Tyr Leu Leu Glu
 65                  70                  75                  80

Glu Ala Thr Leu Gly Met Trp Ala Asp Glu Gln Glu Thr Pro Tyr Val
                 85                  90                  95

Glu Glu Lys Arg Phe Asp Trp Phe Arg Gly Tyr His Val Gly Gly Arg
            100                 105                 110

Ser Leu Leu Trp Gly Arg Gln Thr Tyr Arg Trp Ser Gln Thr Asp Phe
```

```
            115                 120                 125
Glu Ala Asn Ala Lys Glu Gly Ile Ala Val Asp Trp Pro Ile Arg Tyr
130                 135                 140

Gln Asp Val Ala Pro Trp Tyr Asp Tyr Val Glu Arg Phe Ala Gly Ile
145                 150                 155                 160

Ser Gly Ser Lys Glu Gly Leu Asp Ile Leu Pro Asp Gly Glu Phe Leu
                165                 170                 175

Pro Pro Ile Pro Leu Asn Cys Val Glu Glu Asp Val Ala Arg Arg Leu
            180                 185                 190

Lys Asp Arg Phe Lys Gly Thr Arg His Leu Ile Asn Ser Arg Cys Ala
        195                 200                 205

Asn Ile Thr Gln Glu Leu Pro Asp Gln Asp Arg Thr Arg Cys Gln Phe
    210                 215                 220

Arg Asn Lys Cys Arg Leu Gly Cys Pro Phe Gly Gly Tyr Phe Ser Thr
225                 230                 235                 240

Gln Ser Ser Thr Leu Pro Ala Ala Val Ala Thr Gly Asn Leu Thr Leu
                245                 250                 255

Arg Pro Phe Ser Ile Val Lys Glu Ile Leu Tyr Asp Lys Asp Lys Lys
            260                 265                 270

Lys Ala Arg Gly Val Glu Ile Ile Asp Ala Glu Thr Asn Met Thr Tyr
        275                 280                 285

Glu Tyr Thr Ala Asp Ile Ile Phe Leu Asn Ala Ser Thr Leu Asn Ser
    290                 295                 300

Thr Trp Val Leu Met Asn Ser Ala Thr Asp Val Trp Glu Gly Gly Leu
305                 310                 315                 320

Gly Ser Ser Ser Gly Glu Leu Gly His Asn Val Met Asp His His Phe
                325                 330                 335

Arg Met Gly Ala Thr Gly Glu Val Glu Gly Phe Asp Glu Phe Tyr Phe
            340                 345                 350

Lys Gly Arg Arg Pro Ala Gly Phe Tyr Ile Pro Arg Phe Arg Asn Ile
        355                 360                 365

Gly Asp Glu Lys Arg Lys Tyr Leu Arg Gly Phe Gly Tyr Gln Gly Ser
    370                 375                 380

Ala Ser Arg Ser Arg Trp Glu Arg Glu Ile Ala Glu Met Asn Ile Gly
385                 390                 395                 400

Ala Asp Tyr Lys Asp Ala Leu Thr Glu Pro Gly Gly Trp Thr Ile Gly
                405                 410                 415

Met Thr Ala Phe Gly Glu Met Leu Pro Tyr His Glu Asn Arg Val Lys
            420                 425                 430

Leu Asp Gln Asn Lys Lys Asp Lys Trp Gly Leu Pro Val Leu Ser Met
        435                 440                 445

Asn Val Glu Leu Lys Gln Asn Glu Leu Asp Met Arg Glu Asp Met Val
    450                 455                 460

Asn Asp Ala Val Glu Met Phe Glu Ala Val Gly Ile Lys Asn Val Lys
465                 470                 475                 480

Pro Thr Arg Gly Ser Tyr Ala Pro Gly Met Gly Ile His Glu Met Gly
                485                 490                 495

Thr Ala Arg Met Gly Arg Asp Pro Lys Ser Ser Val Leu Asn Gly Asn
            500                 505                 510

Asn Gln Val Trp Asp Ala Pro Asn Val Phe Val Thr Asp Gly Ala Cys
        515                 520                 525

Met Thr Ser Ala Ala Cys Val Asn Pro Ser Leu Thr Tyr Met Ala Leu
530                 535                 540
```

```
Thr Ala Arg Ala Ala Asp Phe Ala Val Ser Glu Leu Lys Lys Gly Asn
545                 550                 555                 560
Leu
```

SOIL MICROORGANISM, NOVEL OXIDOREDUCTASE SEPARATED FROM THE SOIL MICROORGANISM, GENE ENCODING THE OXIDOREDUCTASE, AND METHOD FOR PRODUCING AGLYCONES USING THE MICROORGANISM, THE OXIDOREDUCTASE AND THE GENE

CROSS-REFERENCE TO RELATED APPLICATION

This application is a continuation of U.S. patent application Ser. No. 13/704,210, filed on Dec. 13, 2012, which claims priority to PCT Application No. PCT/KR2011/004361, filed on Jun. 14, 2011, which claims priority to Korean Patent Application No. 10-2010-0066307, filed on Jul. 9, 2010 and Korean Patent Application No. 10-2010-0055988, filed on Jun. 14, 2010, and all the benefits accruing therefrom under 35 U.S.C. §119, the contents of which in its entirety are herein incorporated by reference.

TECHNICAL FIELD

The present disclosure relates to a novel microorganism isolated from soil, an oxidoreductase isolated from the microorganism and a method for deglycosylating various plant glycosides and producing various aglycones using same.

BACKGROUND ART

Ginseng (*Panax ginseng* C. A. Meyer) is one of the herbs that have been traditionally used in Asian countries including Korea, China and Japan for treatment and prevention of a variety of diseases. *Ginseng* saponins also called ginsenosides are main active ingredients of *ginseng* and are known to have various physiological activities including anti-aging activity, anti-inflammatory activity, antioxidative activity in the central nervous system, cardiovascular system and immune system, anti-diabetic activity and antitumor activity.

Until now, more than 40 kinds of ginsenosides have been isolated and identified. The ginsenosides which are glycosides having a dammarane structure including aglycones may be largely classified into protopanaxadiols and protopanaxatriols. The ginsenosides belonging to the protopanaxadiol group are mainly Rb1, Rb2, Rc and Rd, and the ginsenosides belonging to the protopanaxatriol group are mainly Re and Rg1 (see FIG. 1 and FIG. 2).

After taken in, the ginsenosides are metabolized by intestinal microorganisms and the metabolic products are known to have various physiological activities. For example, the representative protopanaxadiol-based saponins Rb1, Rb2 and Rc are metabolized by human intestinal microorganisms to CK and the protopanaxatriol-based saponins Re and Rg1 are metabolized by intestinal microorganisms to Rh1 or F1, thereby exhibiting a variety of physiological activities. CK is known to induce anti-metastatic or anticancer effect of preventing invasion and formation of tumors. And, it is reported that its aglycone PPD(S) has higher physiological activity as compared to the sugar-attached counterpart Rh2.

Accordingly, studies have been made to transform ginsenosides into metabolites having less sugar. In addition to enzymatic methods, hydrolysis using weak acids, degradation using alkalis, or the like have been reported. However, since these methods induce several side reactions such as epimerization, hydration, hydroxylation, etc., methods of transforming into active ginsenosides using enzymes, intestinal microorganisms, and so forth are studied recently. But, most of the reported microorganisms are anaerobic intestinal microorganisms, there is a limit in industrial application. Also, since most enzymes lack the activity of transforming ginsenosides into aglycones and have their own specificity, they are applicable to production of specific ginsenosides only.

Although a lot of studies have been made thus far about the biotransformation of the metabolite of the ginsenoside Rb1 by intestinal microorganisms to CK, there are few researches about production of its aglycone. And, it is reported that the ginsenoside having one sugar on the saponin backbone is not degraded by the enzymes of microorganisms any more. Ginsenosides in aglycone form are known to be absorbed more easily into the bloodstream and act as active compounds. Also, the production of aglycones as backbones of various ginsenosides will make a base technology for specific production of desired types of ginsenoside. Accordingly, there is a need of exploring enzymes involved in the production of ginsenoside aglycones.

DISCLOSURE

Technical Problem

The present disclosure is directed to providing a novel microorganism, a novel oxidoreductase exhibiting deglycosylation activity isolated from the microorganism and a method for producing various ginsenoside aglycones, isoflavone aglycones or flavonoid aglycones using a gene and a recombinant protein encoding same.

Technical Solution

In one general aspect, there is provided novel *Rhizobium* sp. GIN611 (KCTC 11708BP) or a cell extract thereof.

In another general aspect, there is provided a method for deglycosylating a natural product using *Rhizobium* sp. GIN611 or a cell extract thereof as a biocatalyst.

In another general aspect, there is provided a method for producing aglycones from various glycosides using *Rhizobium* sp. GIN611 or a cell extract thereof as a biocatalyst.

In another general aspect, there is provided an oxidoreductase having an amino acid sequence of SEQ ID NO 3 or a cell extract including same.

In another general aspect, there is provided a DNA encoding an oxidoreductase having an amino acid sequence of SEQ ID NO 3, a DNA having a sequence of SEQ ID NO 2, a recombinant DNA vector including the DNA having a sequence of SEQ ID NO 2, a host cell transformed with the recombinant DNA vector including the DNA having a sequence of SEQ ID NO 2 or a cell extract including the host cell transformed with the recombinant DNA vector including the DNA having a sequence of SEQ ID NO 2

In another general aspect, there is provided an oxidoreductase having a sequence identity of at least 60% with a sequence of SEQ ID NO 3 and having a deglycosylation activity or a cell extract including the oxidoreductase.

In another general aspect, there is provided a method for deglycosylating a natural product using a biocatalyst selected from a group consisting of an oxidoreductase having an amino acid sequence of SEQ ID NO 3, a cell extract including the oxidoreductase having an amino acid sequence of SEQ ID NO 3, a host cell transformed with a recombinant DNA vector including a DNA encoding the oxidoreductase having an amino acid sequence of SEQ ID NO 3, a cell extract including the host cell transformed with a recombinant DNA vector including a DNA encoding the oxidoreductase having an amino acid sequence of SEQ ID NO 3, a host cell transformed with a recombinant DNA vector including a DNA having a sequence of SEQ ID NO 2, a cell extract of the host cell transformed with a recombinant DNA vector including a DNA having a sequence of SEQ ID NO 2, a host cell transformed with a recombinant DNA vector including a DNA encoding a protein having a sequence identity of at least 60% with a sequence of SEQ ID NO 3 and having deglycosylation activity, a cell extract including the host cell transformed with a recombinant DNA vector including a DNA encoding a protein having a sequence identity of at least 60% with a sequence of SEQ ID NO 3 and having deglycosylation activity, an oxidoreductase having a sequence identity of at least 60% with a sequence of SEQ ID NO 3 and having deglycosylation activity, and a cell extract including the oxidoreductase having a sequence identity of at least 60% with a sequence of SEQ ID NO 3 and having deglycosylation activity.

In another general aspect, there is provided a method for producing aglycones from various glycosides using a biocatalyst selected from a group consisting of an oxidoreductase having an amino acid sequence of SEQ ID NO 3, a cell extract including the oxidoreductase having an amino acid sequence of SEQ ID NO 3, a host cell transformed with a recombinant DNA vector including a DNA encoding the oxidoreductase having an amino acid sequence of SEQ ID NO 3, a cell extract including the host cell transformed with a recombinant DNA vector including a DNA encoding the oxidoreductase having an amino acid sequence of SEQ ID NO 3, a host cell transformed with a recombinant DNA vector including a DNA having a sequence of SEQ ID NO 2, a cell extract of the host cell transformed with a recombinant DNA vector including a DNA having a sequence of SEQ ID NO 2, a host cell transformed with a recombinant DNA vector including a DNA encoding a protein having a sequence identity of at least 60% with a sequence of SEQ ID NO 3 and having deglycosylation activity, a cell extract including the host cell transformed with a recombinant DNA vector including a DNA encoding a protein having a sequence identity of at least 60% with a sequence of SEQ ID NO 3 and having deglycosylation activity, an oxidoreductase having a sequence identity of at least 60% with a sequence of SEQ ID NO 3 and having deglycosylation activity, and a cell extract including the oxidoreductase having a sequence identity of at least 60% with a sequence of SEQ ID NO 3 and having deglycosylation activity.

In another general aspect, there is provided a method for preparing a cell extract of *Rhizobium* sp. GIN611, a cell extract including an oxidoreductase having an amino acid sequence of SEQ ID NO 3, a cell extract including a host cell transformed with a recombinant DNA vector including a DNA encoding an oxidoreductase having an amino acid sequence of SEQ ID NO 3, a cell extract including a host cell transformed with a recombinant DNA vector including a DNA having a sequence of SEQ ID NO 2, or a cell extract including an oxidoreductase having a sequence identity of at least 60% with a sequence of SEQ ID NO 3 and having deglycosylation activity, including inducing enzymatic expression by adding a ginsenoside.

Advantageous Effects

In general, ginsenoside-deglycosylating enzymes are known to belong to the glucosidase family. The inventors of the present disclosure have found that an enzyme belonging to the oxidoreductase family, not to the glucosidase family, has a deglycosylation activity for ginsenosides. This novel oxidoreductase is entirely different from the previously known deglycosylating enzymes in sequence, has a sequence similarity with the enzymes in the oxidoreductase family, and induces spontaneous deglycosylation by oxidizing a sugar in a naturally occurring glycoside.

DESCRIPTION OF DRAWINGS

FIG. 8 shows a 16S DNA sequence of a novel soil microorganism *Rhizobium* sp. GIN611 growing with a ginsenoside as a carbon source.

Figure 9:
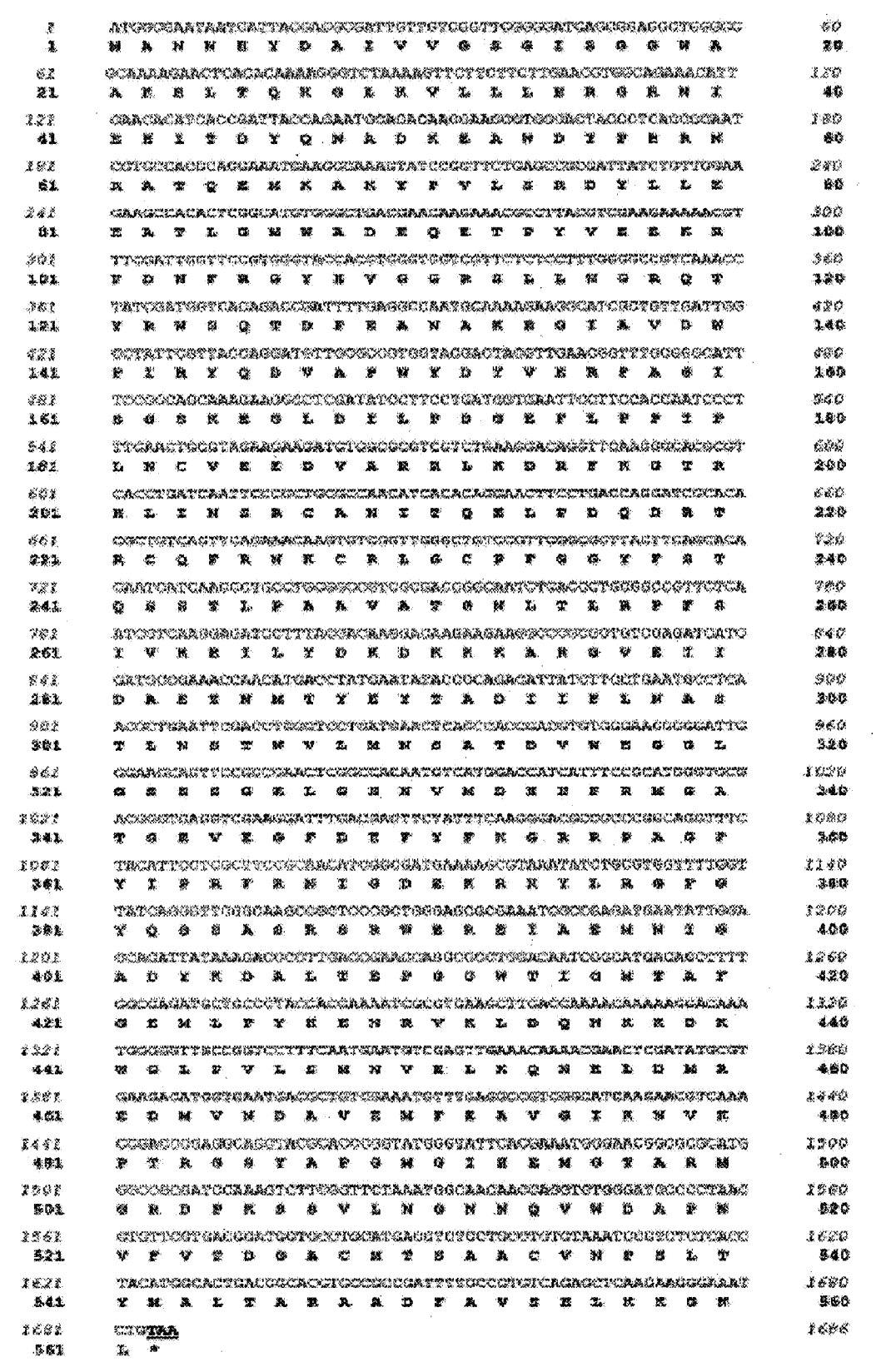

FIG. 9 shows an amino acid sequence of an oxidoreductase produced by *Rhizobium* sp. GIN611 and a sequence of a gene encoding same.

BEST MODE

Figure 1:
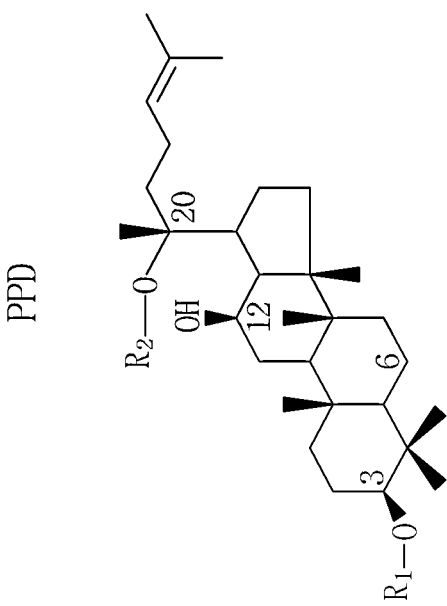
FIG. 1 shows a protopanaxadiol (PPD)-based ginsenoside.
Figure 2:
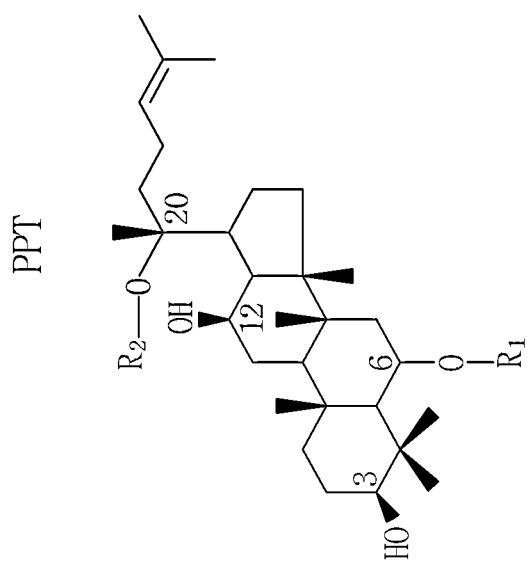
FIG. 2 shows a protopanaxatriol (PPT)-based ginsenoside.

The terms used in the present disclosure are those commonly used in the related art and may be easily understood by those skilled in the art. Some of them will be described briefly.

(1) Ginsenoside: *ginseng* saponin; the active ingredient of *ginseng*.
(2) Compound K (CK): 20-O-β-D-glucopyranosyl-20(S)-protopanaxadiol.
(3) Ginsenoside Rh2: 3-O-β-D-glycopyranosyl-20(S)-protopanaxadiol.
(4) Ginsenoside F2: 3-O-(β-D-glucopyranosy)-20-O-(β-D-glucopyranosyl)-20(S)protopanaxadiol.
(5) Ginsenoside Rb1: 3-O-[(β-D-glucopyranosy)(1,2)-β-D-glucopyranosyl]-20-O-[(β-D-glucopyranosyl)(1,6)-β-D-glucopyranosyl]-20(S)protopanaxadiol.
(6) Ginsenoside Rb2: 3-O-[(β-D-glucopyranosy)(1,2)-β-D-glucopyranosyl]-20-O-[(α-L-arabinopyranosyl)(1,6)-β-D-glucopyranosyl)]-20(S)protopanaxadiol.
(7) Ginsenoside Rc: 3-O-[(β-D-glucopyranosy)(1,2)-β-D-glucopyranosyl)]-20-O-[(α-L-arabinofuranosyl)(1,6)-β-D-glucopyranosyl)]-20(S)protopanaxadiol.

(8) Ginsenoside Rb3: 3-O-[(β-D-glucopyranosy)(1,2)-β-D-glucopyranosyl]-20-O-[(β-D-xylopyranosyl)(1,6)-β-D-glucopyranosyl]-20(S)protopanaxadiol.
(9) Ginsenoside F1: 20-O-β-D-glucopyranosyl-20(S)-protopanaxadiol.
(10) Ginsenoside Re: 6-O-[(α-L-rhamnopyranosyl(1,2)-β-D-glucopyranosyl]-20-O-(β-D-glucopyranosyl)-20(S)-protopanaxatriol.
(11) Daidzin: daidzein 7-O-β-D-glucoside.
(12) PPD(S): 20(S)-protopanaxadiol.
(13) Compound Y: 20-O-[(α-L-arabinopyranosyl)(1,6)-β-D-glucopyranosyl]-20(S)protopanaxadiol.
(14) Compound Mc: 20-O-[(α-L-arabinofuranosyl)(1,6)-β-D-glucopyranosyl]-20(S)protopanaxadiol.
(15) Compound Mx: 20-O-[(β-D-xylopyranosyl)(1,6)-β-D-glucopyranosyl]-20(S)protopanaxadiol.
(16) PPT(S): 20(S)-protopanaxatriol.
(17) Ginsenoside Rg2: 6-O-[(α-L-rhamnopyranosyl(1,2)-β-D-glucopyranosyl]-20(S)-protopanaxatriol.
(18) Daidzein: 7-hydroxy-3-(4-hydroxyphenyl)chromen-4-one.
(19) Icariin: 3,4',5,7-tetrahydroxy-8-prenylflavone-4'-Me ether-3-O-alpha-L-rhamnopyranoside, 7-O-beta-D-glucopyranoside.
(20) Camelliaside A: kaempferol 3-O-(2-O-galactopyranosyl-6-O-rhamnopyranosyl)glucopyranoside.
(21) Camelliaside B: kaempferol 3-O-(2-O-xylopyranosyl-6-O-rhamnopyranosyl)glucopyranoside.
(22) Glycone(s): sugar molecule(s) attached to a glycoside.
(23) Whole-cell reaction: a reaction using whole cells without disrupting the cells or isolating enzymes.
(24) Oxidoreductase: an enzyme that catalyzes oxidation and reduction reactions necessary for providing energy to an organism. Most of oxidation of organic compounds occurs by dehydrogenation.
(25) Oxidoreductase extract: a cell extract comprising an oxidoreductase which is obtained disrupting the cells of *Rhizobium* sp. GIN611 or recombinant proteins expressing the oxidoreductase.
(22) MALDI-TOF mass spectrometry: matrix-assisted laser desorption/Ionization time-of-flight mass spectrometry.
(26) HPLC: high-performance liquid chromatography.
(27) PCR: polymerase chain reaction; a technique of specifically amplifying a region of a DNA.
(28) ORF: open reading frame; a sequence between an initiation codon and a stop codon.
(29) Cloning: a technique of inserting a DNA fragment into a recombinant DNA cloning vector and transforming a host cell using the resulting recombinant DNA.
(30) bp: base pair(s).

The present disclosure provides novel microorganism *Rhizobium* sp. GIN611 or a cell extract thereof. The inventors of the present disclosure have selected the microorganism which grows with a mixture of various ginsenosides as a carbon source and have confirmed that the microorganism has reactivity for ginsenoside CK as substrate.

In an embodiment, the present disclosure provides a method for deglycosylating a natural product using *Rhizobium* sp. GIN611 or a cell extract thereof as a biocatalyst.

The natural product may be a ginsenoside glycoside, an isoflavone glycoside or a flavonoid glycoside, but is not limited thereto.

In another embodiment, the present disclosure provides a method for producing various aglycones from glycosides using *Rhizobium* sp. GIN611 or a cell extract thereof as a biocatalyst.

The glycoside may be a ginsenoside glycoside, an isoflavone glycoside or a flavonoid glycoside, but is not limited thereto.

The aglycone may be a ginsenoside aglycone, an isoflavone aglycone or a flavonoid aglycone, but is not limited thereto.

The ginsenoside glycoside is not specially limited but may be selected, for example, from a group consisting of ginsenoside compound K (CK), ginsenoside Rh2, ginsenoside F2, ginsenoside Rb1, ginsenoside Rb2, ginsenoside Rc, ginsenoside Rb3, ginsenoside F1, and ginsenoside Re. Specifically, it may be ginsenoside compound K (CK).

The ginsenoside aglycone is not specially limited but may be selected, for example, from a group consisting of ginsenoside PPD(S), ginsenoside compound Y, ginsenoside Mc, ginsenoside compound Mx, ginsenoside PPT(S) and ginsenoside Rg2. Specifically, it may be ginsenoside PPD(S).

The ginsenoside glycosides and ginsenoside aglycones are summarized in Table 1.

TABLE 1

| Ginsenoside glycosides | Ginsenoside aglycones |
|---|---|
| Ginsenoside compound K (CK) | Ginsenoside PPD(S) |
| Ginsenoside Rh2 | Ginsenoside PPD(S) |
| Ginsenoside F2 | Ginsenoside PPD(S) |
| Ginsenoside Rb1 | Ginsenoside PPD(S) |
| Ginsenoside Rb2 | Ginsenoside compound Y |
| Ginsenoside Rc | Ginsenoside Mc |
| Ginsenoside Rb3 | Ginsenoside compound Mx |
| Ginsenoside F1 | Ginsenoside PPT(S) |
| Ginsenoside Re | Ginsenoside Rg2 |

The isoflavone glycoside is not specially limited but may be, for example, daidzin.

The isoflavone aglycone is not specially limited but may be, for example, daidzein.

The flavonoid glycoside is not specially limited but may be, for example, icariin, camelliaside A or camelliaside B.

The deglycosylation is accomplished by oxidizing a sugar of the glycoside of the natural product. For example, if the sugar is glucose, deglycosylation occurs spontaneously by oxidizing the 3-hydroxyl (OH) group of a glucose residue.

The sugar is not specially limited but may be selected from a group consisting of glucose, galactose, rhamnose, arabinose and xylose.

In another embodiment, the present disclosure provides an oxidoreductase comprising an amino acid sequence of SEQ ID NO 3 or a cell extract comprising the oxidoreductase. Specifically, the oxidoreductase may be isolated from *Rhizobium* sp. GIN611.

In another embodiment, the present disclosure provides a DNA sequence encoding an amino acid sequence of SEQ ID NO 3 or a DNA sequence encoding the oxidoreductase. Specifically, the sequence is SEQ ID NO 2. Specifically, the DNA may be a DNA encoding the oxidoreductase isolated from *Rhizobium* sp. GIN611.

In another embodiment, the present disclosure provides a DNA encoding a protein having a sequence identity of at least 60%, specifically at least 90%, more specifically at least 97%, further more specifically at least 99%, with a sequence of SEQ ID NO 3 and having a deglycosylation activity for a natural product. A sugar degraded by the protein may be selected from a group consisting of glucose, galactose, rhamnose, arabinose and xylose.

In another embodiment, the present disclosure provides a recombinant DNA vector comprising a DNA sequence encoding the amino acid sequence of SEQ ID NO 3, a DNA sequence encoding an oxidoreductase comprising the amino acid sequence of SEQ ID NO 3 or a DNA sequence comprising a sequence of SEQ ID NO 2.

In another embodiment, the present disclosure provides a host cell transformed with the recombinant DNA vector and a cell extract comprising the host cell.

In another embodiment, the present disclosure provides an oxidoreductase having a sequence identity of at least 60%, specifically at least 90%, more specifically at least 97%, further more specifically at least 99%, with a sequence of SEQ ID NO 3 and having a deglycosylation activity for a natural product and a cell extract comprising the oxidoreductase.

The oxidoreductase is not specially limited but may be derived from *Agrobacterium* sp., *Sphingobacterium* sp. or *Stenotrophomonas* sp.

In another embodiment, the present disclosure provides a method for deglycosylating a natural product using a biocatalyst selected from a group consisting of an oxidoreductase comprising an amino acid sequence of SEQ ID NO 3, a cell extract comprising the oxidoreductase comprising an amino acid sequence of SEQ ID NO 3, a host cell transformed with a recombinant DNA vector comprising a DNA encoding the oxidoreductase comprising an amino acid sequence of SEQ ID NO 3, a cell extract comprising the host cell transformed with a recombinant DNA vector comprising a DNA encoding the oxidoreductase comprising an amino acid sequence of SEQ ID NO 3, a host cell transformed with a recombinant DNA vector comprising a DNA comprising a sequence of SEQ ID NO 2, a cell extract of the host cell transformed with a recombinant DNA vector comprising a DNA comprising a sequence of SEQ ID NO 2, a host cell transformed with a recombinant DNA vector comprising a DNA encoding a protein having a sequence identity of at least 60% with a sequence of SEQ ID NO 3 and having deglycosylation activity, a cell extract comprising the host cell transformed with a recombinant DNA vector comprising a DNA encoding a protein having a sequence identity of at least 60% with a sequence of SEQ ID NO 3 and having deglycosylation activity, an oxidoreductase having a sequence identity of at least 60% with a sequence of SEQ ID NO 3 and having deglycosylation activity, and a cell extract comprising the oxidoreductase having a sequence identity of at least 60% with a sequence of SEQ ID NO 3 and having deglycosylation activity.

In another embodiment, the present disclosure provides a method for producing various aglycones of a natural product using a biocatalyst selected from a group consisting of an oxidoreductase comprising an amino acid sequence of SEQ ID NO 3, a cell extract comprising the oxidoreductase comprising an amino acid sequence of SEQ ID NO 3, a host cell transformed with a recombinant DNA vector comprising a DNA encoding the oxidoreductase comprising an amino acid sequence of SEQ ID NO 3, a cell extract comprising the host cell transformed with a recombinant DNA vector comprising a DNA encoding the oxidoreductase comprising an amino acid sequence of SEQ ID NO 3, a host cell transformed with a recombinant DNA vector comprising a DNA comprising a sequence of SEQ ID NO 2, a cell extract of the host cell transformed with a recombinant DNA vector comprising a DNA comprising a sequence of SEQ ID NO 2, a host cell transformed with a recombinant DNA vector comprising a DNA encoding a protein having a sequence identity of at least 60% with a sequence of SEQ ID NO 3 and having deglycosylation activity, a cell extract comprising the host cell transformed with a recombinant DNA vector comprising a DNA encoding a protein having a sequence identity of at least 60% with a sequence of SEQ ID NO 3 and having deglycosylation activity, an oxidoreductase having a sequence identity of at least 60% with a sequence of SEQ ID NO 3 and having deglycosylation activity, and a cell extract comprising the oxidoreductase having a sequence identity of at least 60% with a sequence of SEQ ID NO 3 and having deglycosylation activity. Specifically, the method is a method for producing aglycones from various glycosides using a biocatalyst, more specifically, a method for producing a ginsenoside aglycone, an isoflavone aglycone or a flavonoid aglycone from a ginsenoside glycoside, an isoflavone glycoside or a flavonoid glycoside.

In another embodiment, the present disclosure provides a method for preparing a cell extract of *Rhizobium* sp. GIN611, a cell extract comprising an oxidoreductase comprising an amino acid sequence of SEQ ID NO 3, a cell extract comprising a host cell transformed with a recombinant DNA vector comprising a DNA encoding an oxidoreductase comprising an amino acid sequence of SEQ ID NO 3, a cell extract comprising a host cell transformed with a recombinant DNA vector comprising a DNA comprising a sequence of SEQ ID NO 2, a cell extract comprising a host cell transformed with a recombinant DNA vector comprising a DNA encoding a protein having a sequence identity of at least 60% with a sequence of SEQ ID NO 3 and having deglycosylation activity, or a cell extract comprising an oxidoreductase having a sequence identity of at least 60% with a sequence of SEQ ID NO 3 and having deglycosylation activity, comprising inducing enzymatic expression by adding a ginsenoside.

Selection of Microorganism Comprising Enzyme Having Deglycosylation Activity for Ginsenoside The inventors of the present disclosure have selected a soil microorganism comprising an enzyme having activity for ginsenoside CK from soil using a minimal medium comprising a mixture of ginsenosides as a carbon source, as described in Table 2. Table 2 shows the composition of the minimal medium comprising a mixture of ginsenosides as a carbon source.

TABLE 2

| | Ingredients | Contents |
|---|---|---|
| Carbon source | Ginsenoside mixture (red ginseng extract) | 0.2%, w/v |
| Nitrogen source | NH$_4$Cl | 1 g/L |
| Buffer ingredient | 64 g Na$_2$HPO$_4$•7H$_2$O | 12.8 g/L |
| | 15 g KH$_2$PO$_4$ | 3 g/L |
| Trace ingredient | 2.5 g NaCl | 0.5 g/L |
| | MgSO$_4$ | 1 mM |
| | CaCl$_2$ | 0.1 mM |
| Solid ingredient | Agar | 1-3% |

The method of selecting the microorganism using the minimal medium is a simple method based on growth rate. During the culturing, the microorganisms having low deglycosylation activity are removed spontaneously and only the microorganism comprising the enzyme with high activity remains.

Thus selected microorganism is a novel one. The inventors have identified that it belongs to the genus *Rhizobium* based on the characteristic DNA sequence encoding the 16S rRNA sequence and named it *Rhizobium* sp. GIN611. They have deposited the microorganism in the Korean Collection for Type Cultures (KCTC) on Jun. 4, 2010 (KCTC 11708BP).

Investigation of the substrate specificity using a deglycosylating enzyme isolated from the selected *Rhizobium* sp. GIN611 revealed that the microorganism exhibits high activity for ginsenoside CK and has deglycosylation activity for other various ginsenosides. The inventors of the present disclosure have disrupted and centrifuged the microorganism and produced a cell extract comprising the active enzyme from a supernatant.

Production of Ginsenoside Aglycone Using Deglycosylating Enzyme Extract as Biocatalyst Aglycone PPD(S) may be produced from a reaction solution comprising the microorganism or the deglycosylating enzyme extract and ginsenoside CK. The associated reaction is initiated by adding the microorganism or the enzyme extract to the reaction solution as a biocatalyst.

In addition to the ginsenoside CK, a PPD-based ginsenoside such as ginsenoside Rb1, ginsenoside Rb2, ginsenoside Rb3, ginsenoside Rc, ginsenoside Rd, ginsenoside F2 and ginsenoside Rh2 may be used as the substrate. As a PPT-based ginsenoside, ginsenoside Re or ginsenoside F1 may be used. Also, the isoflavone daidzin and the flavonoids icariin, camelliaside A or camelliaside B may be used.

Hereinafter, the present disclosure is described in further detail through examples. The examples are for illustrative purposes only. It will be appreciated by those of ordinary skill in the art that and are not intended to limit the scope of this disclosure.

Example 1

Selection of *Rhizobium* sp GIN611

A soil sample (10 g) was added to phosphate buffered saline (PBS; 50 mL) and stirred at room temperature for 2 hours. The resulting turbid mixture was passed through filter paper to remove suspending matter. The filtered microorganism solution (0.2 mL) was added to the minimal medium (10 mL) described in Table 2 and incubated at 30° C. for 3 days. After repeating this procedure 3 times, the culture solution (0.2 mL) was transferred to a solid minimal medium consisting of the liquid minimal medium and 1.5% agar and incubated at 30° C. for 24 hours. After incubating each 3 mL of microorganism in the liquid minimal medium and reacting, respectively, the colony exhibiting high activity for ginsenoside CK was identified as *Rhizobium* sp.

Example 2

Preparation of Deglycosylating Enzyme Extract

Cells cultured in a medium (hereinafter, a complete medium) consisting of yeast extract (5 g/L), peptone (10 g/L) and sodium chloride (10 g/L) were washed 3 times with PBS buffer (pH 7.0) and the medium components other than the cells were removed. The recovered cells were suspended in 5 cell volume equivalents of a buffer solution (hereinafter, a lysis buffer) consisting of 5 cell volume equivalents of 20 mM phosphate buffer, 1 mM ethylenediaminetetraacetic acid (EDTA), 1 mM phenylmethanesulfonyl fluoride (PMSF) and 1 mM dithiothreitol (DTT). After disrupting the cells using an ultrasonic homogenizer, followed by centrifugation at 13,000 rpm for 30 minutes, the supernatant was recovered and a deglycosylating enzyme extract was obtained.

Example 3

Inducement of Expression of Deglycosylating Enzyme by Addition of Ginsenoside

Cells cultured using the liquid minimal medium (hereinafter, M9/ginsenoside medium) described in Table 2 were washed 3 times with PBS buffer and the medium components other than the cells were removed. The recovered cells were suspended in a lysis buffer. After disrupting the cells using an ultrasonic homogenizer, followed by centrifugation at 13,000 rpm for 30 minutes, the supernatant was recovered and a cell extract comprising a deglycosylating enzyme which was induced to express in the minimal medium was obtained.

Example 4

Figure 6:
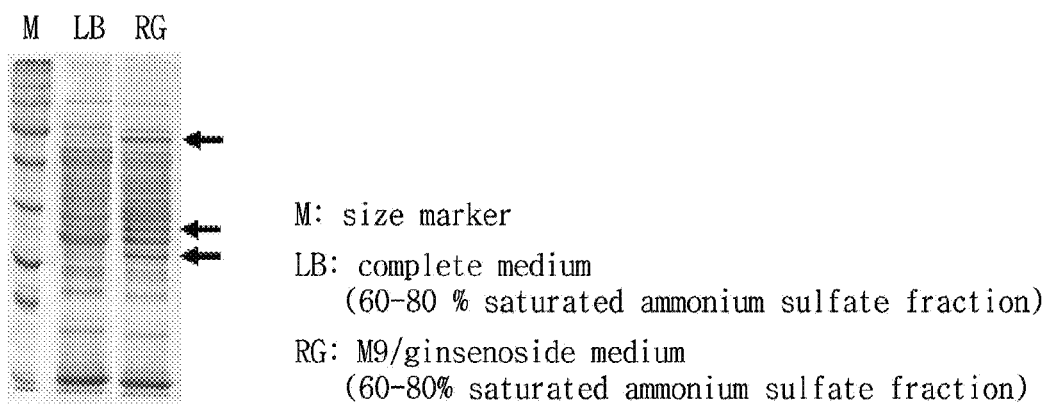
FIG. 6 compares SDS-polyacrylamide gel electrophoresis result of proteins expressed in a complete medium and an M9/ginsenoside medium.
Figure 7:
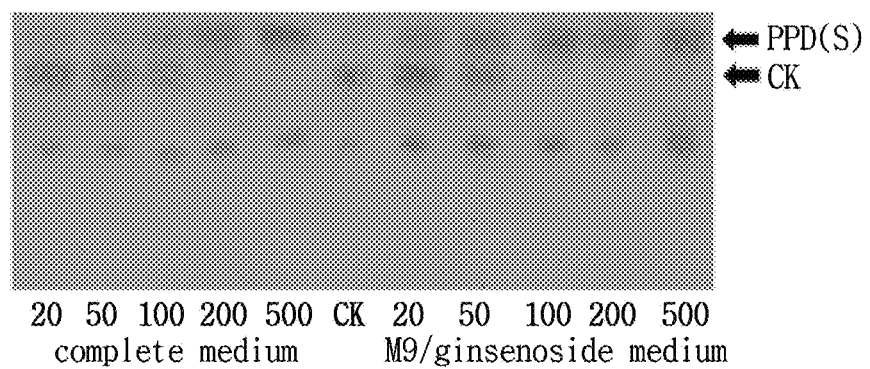
FIG. 7 shows a result of comparing reactivity of proteins obtained from cells cultured in a complete medium and an M9/ginsenoside medium.

Comparison of Reactivity and Expression Level of Proteins Prepared in Complete Medium and M9/Ginsenoside Medium After quantitating the amount of proteins in the cell extracts prepared in Example 2 and Example 3, reactivity for ginsenoside CK was compared using the same amount of proteins. As a result, the cell extract prepared in Example 3 exhibited higher reactivity than the cell extract prepared in Example 2 (see FIG. 7). After reaction using the same amount of proteins, the reactivity was compared as per amount of proteins. Whereas the protein obtained from the cells cultured in the complete medium (Example 2) resulted in complete conversion from ginsenoside CK to PPD(S) when 500 or more of protein was used, the protein obtained from the cells cultured in the M9/ginsenoside medium (Example 3) resulted in conversion from ginsenoside CK to PPD(S) when 100 or more of protein was used. Also, expression level of the proteins from the two extracts was compared by sodium dodecyl sulfate polyacrylamide gel electrophoresis (SDS-PAGE). The result is shown in FIG. 6. In FIG. 6, the arrows indicate that the proteins whose expression level is different in the enzyme extracts of Example 2 and Example 3.

Example 5

Isolation and Purification of Deglycosylating Enzyme

Figure 3:
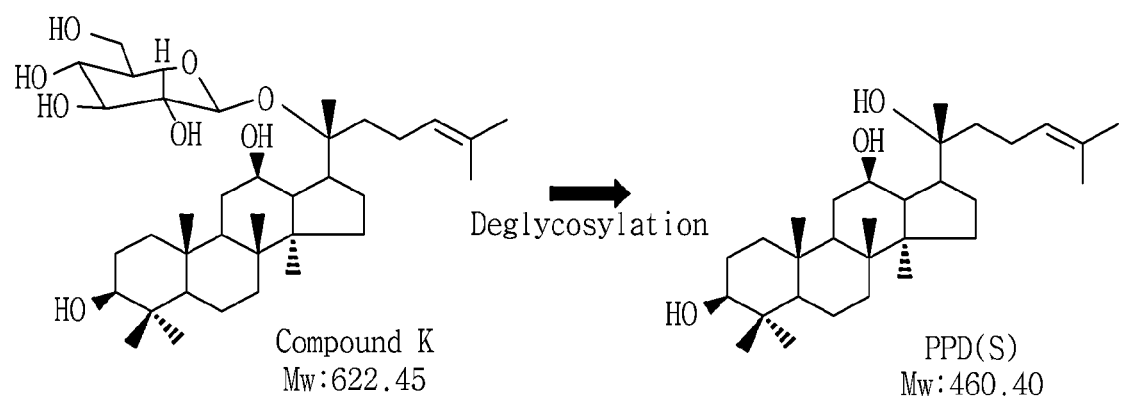
FIG. 3 describes a reaction whereby an aglycone PPD(S) is produced from a ginsenoside compound K (CK) by deglycosylation.

In order to isolate the enzyme catalyzing the reaction illustrated in FIG. 3 from the novel *Rhizobium* sp. GIN611, the microorganism was cultured in the liquid minimal medium described in Table 2 after adding a ginsenoside (10 L). Then, an enzyme extract was prepared from the cultured microorganism in the same manner as described in Example 2. The prepared enzyme extract was subjected to 60-70% saturated ammonium sulfate fractionation. Thus obtained proteins were isolated and purified by fast protein liquid chromatography (FPLC) using several columns. The reactivity of the purified protein was investigated by native gel electrophoresis.

Example 6

Activity of Purified Enzyme for Ginsenoside CK

Figure 4:
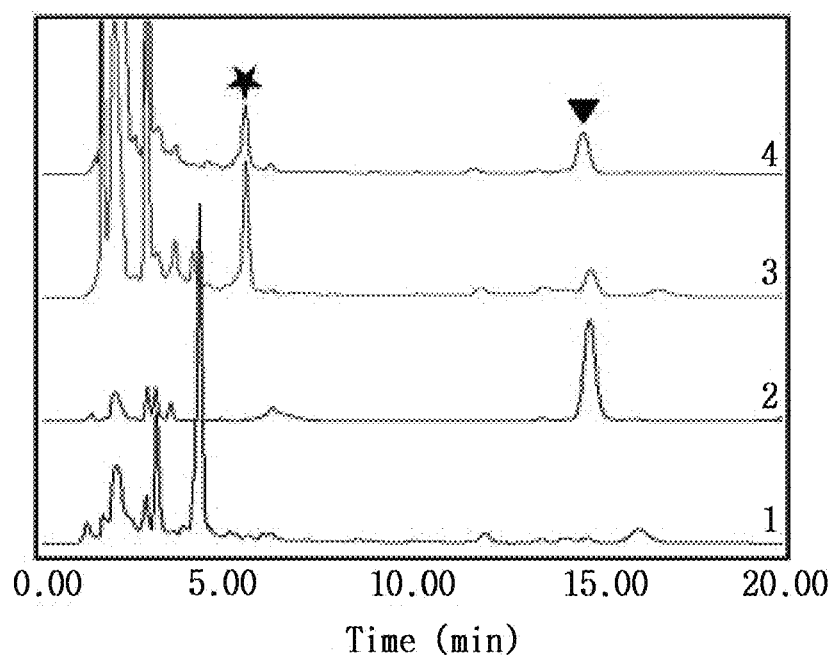
FIG. 4 shows a reactivity analysis result of a novel oxidoreductase. The asterisk indicates oxidized CK and the triangle indicates PPD(S). The chromatogram 3 shows a result of reaction for 3 hours and the chromatogram 4 shows a result of reaction for 12 hours. The amount of the substrate CK decreases with time, that of the intermediate, oxidized CK, increase and then decreases, and that of the final product PPD(S) increases consistently with time.
Figure 5:
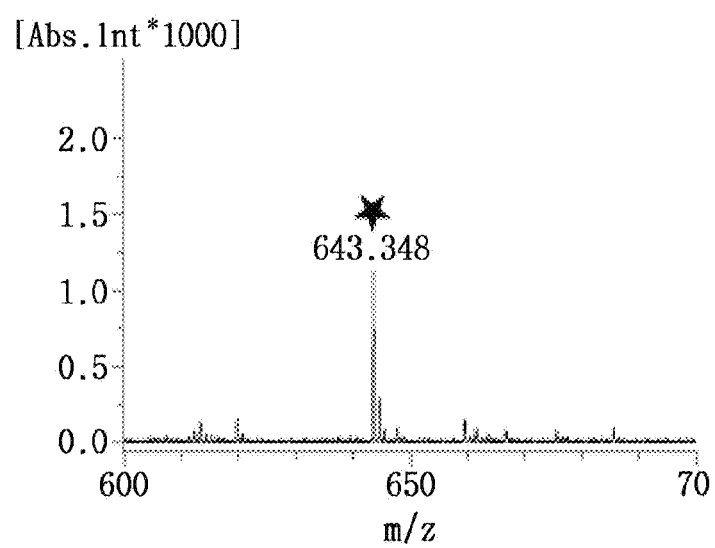
FIG. 5 shows a mass analysis result of oxidized CK analyzed in FIG. 4.
Figure 10:
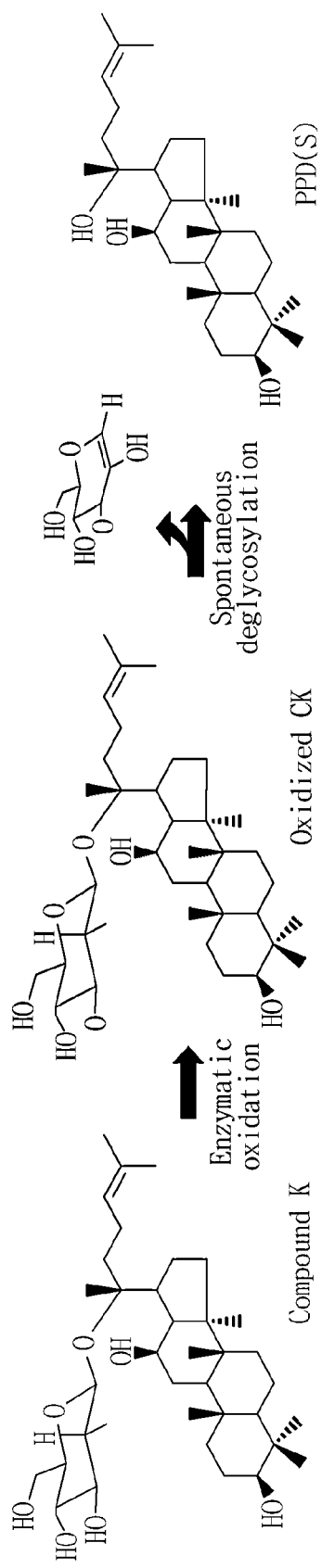
FIG. 10 shows a reaction mechanism of a novel oxidoreductase.
Figure 11:
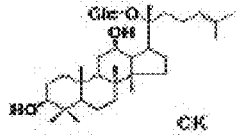
FIG. 11 shows a reactivity analysis result of a novel oxidoreductase for various ginsenosides and isoflavone. It can be seen that the enzyme has specific reactivity for glucose.

The activity of the enzyme purified in Example 5 for ginsenoside CK was investigated. A reaction was performed by using about 100 μg enzyme solution, 0.1 mM CK and 50 mM phosphate buffer(pH 6.5), and adding ethyl acetate of the same volume as that of the solution. After the reaction is completed, HPLC analysis was performed by isocratic elution using 80% acetonitrile (ACN). The result is shown in FIG. 4. In the figure, the peak indicated by the triangle is that of PPD(S) and the peak indicated by the asterisk is that of oxidized CK. It can be seen that the amount of oxidized CK increase and then decreases with time and that of PPD(S) increases consistently. This suggests that the sugar is degraded by the novel enzyme through oxidation of ginsenoside CK. The reaction mechanism is illustrated in FIG. 10.

Example 7

Determination of N-Terminal and Internal Peptide Sequences of Novel Enzyme

The N-terminal amino acid sequence of the oxidoreductase purified in Example 5 was determined by Edman sequencing using the Procise 491 sequencer (Applied Biosystems, CA) using Edman analytic technique after performing 12% SDS-PAGE electrophoresis, transferring the fragments to PVDF membrane (Bio-Rad). The sequence of the internal peptide was determined using the PEAKS software after analyzing the sequence of the peptide fragments obtained by treating with trypsin for sequencing (Promega) using the LTQ-Orbitrap mass analyzer.

Example 8

Isolation of Total DNA from Rhizobium sp. GIN611

Cells cultured in the complete medium were centrifuged at 4° C. and 4,000 rpm for 10 minutes and precipitated. After removing the supernatant, the remaining cells were lysed in 10 mL of lysis buffer (15% sucrose, 25 mM EDTA, 25 mM Tris buffer) and left at 37° C. for 10 minutes after adding 1.2 mL of EDTA (0.5 M) and 0.13 mL of Pronase. Then, after adding 10% SDS (1 mL), the mixture was kept at 70° C. for 10 minutes and then in icy water for 10 minutes. Subsequently, reaction was performed for 15 minutes in icy water after adding 5 M potassium acetate (2.5 mL). After adding a phenol/chloroform mixture (50:50) of the same volume to the reaction solution and mixing for 30 minutes, centrifugation was performed at 4° C. and 4,000 rpm for 10 minutes and the supernatant was obtained. After adding 0.5 volume equivalent of chloroform to the resulting solution and mixing slowly, centrifugation was performed at 4° C. and 4,000 rpm for 10 minutes and the supernatant was obtained. Then, after treating with RNase until an amount of 50/mL, followed by incubation at 37° C. for 1 hour, 0.8 volume equivalent of isopropanol was added and then 2.5 volume equivalents of 80% ethanol was added. After gently shaking, total DNA was collected using a Pasteur pipette, transferred to a 1.5 mL microtube, dried and then dissolved in sterilized water for further use.

Example 9

Gene Sequencing of Deglycosylating Enzyme by PCR

After preparing primers using the N-terminal amino acid sequence and the internal sequence determined in Example 7, DNA fragments of the oxidoreductase were obtained using the genomic DNA obtained in Example 8 as a template. Primers binding specifically to the obtained DNA fragments were prepared and the remaining sequence was determined by inverse PCR. A self-ligated DNA obtained by cutting the genomic DNA fragments using the Hind III restriction enzyme and then treating with ligase was used as a template for inverse PCR.

Example 10

Recombination Expression Vector and Expression in Transformed E. coli

The DNA sequence of the obtained oxidoreductase was digested with the BamHI/SalI restriction enzyme and the resulting fragments were ligated into pETDuet-1 (Novagen) to prepare a recombinant plasmid, which was then transformed E. coli for expression (Rosetta-gami2; DE3). The transformed E. coli was cultured in a medium containing ampicillin. When the optical density reached 0.3-0.7, IPTG was added and expression of the enzyme was induced by further incubating at 20° C. for 15 hours.

Example 11

Deglycosylation Reactivity of Three Enzymes Having Sequence Similarity of at Least 65% with Novel Enzyme of SEQ ID NO 3 for Ginsenoside and Glycoside Derived from Natural Product Enzymes derived from Agrobacterium sp., Sphingobacterium sp. or Stenotrophomonas sp. and having amino acid sequence similarity of at least 60% with SEQ ID NO 3 were cloned and their deglycosylation reactivity for glucose of ginsenosides was investigated. The enzymes derived from the microorganisms were confirmed to degrade the glucose residue of ginsenosides by oxidation.

Example 12

Measurement of Aglycone Production Activity Using Expression-Induced Enzyme

After preparing the enzyme whose expression was induced in Example 11 by the method described in Example 2, aglycone production activity was measured using ginsenoside CK as a substrate.

Example 13

Measurement of Activity Using Various Ginsenosides and Isoflavone as Substrates

After reacting using ginsenoside Rh2, ginsenoside F2, ginsenoside Rb1, ginsenoside Rb2, ginsenoside Rc, ginsenoside Rb3, ginsenoside F1, ginsenoside Re or the isoflavone daidzin as a substrate, followed by extraction by adding the same volume of ethyl acetate, the ethyl acetate layer was dried and then dissolved again in ethanol, which was subjected to activity measurement by MALDI mass spectrometry.

Example 14

Figure 12:
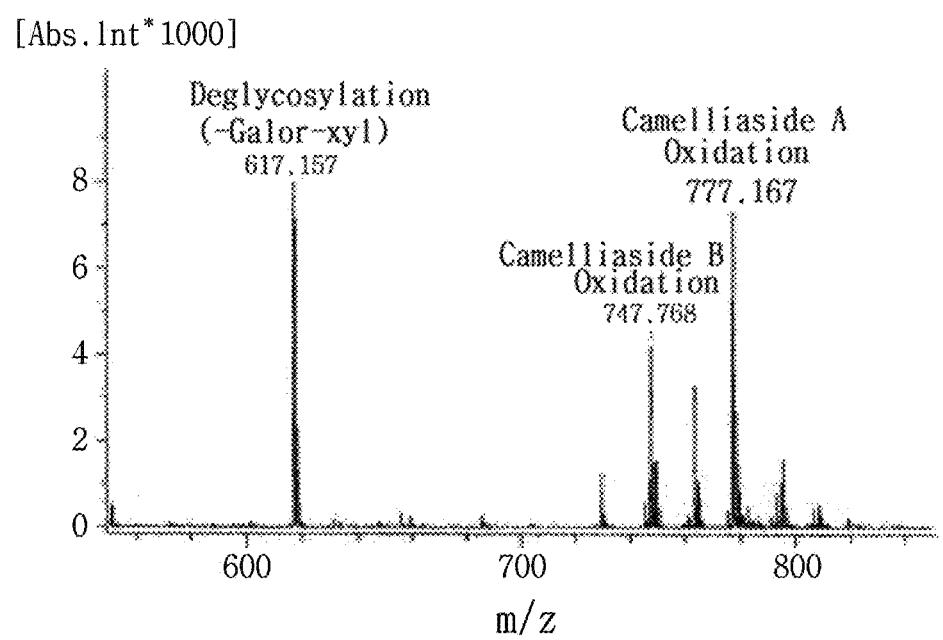
FIG. 12 shows a result of measuring deglycosylation activity of a mixture of camelliaside A and camelliaside B.
Figure 13:
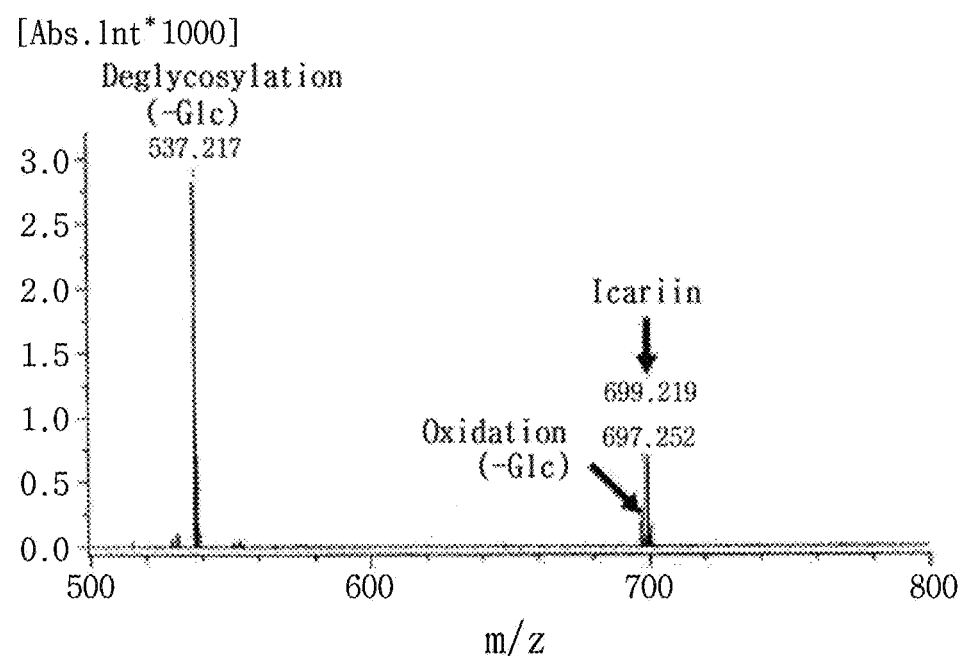
FIG. 13 shows a result of measuring deglycosylation activity of icariin.

Measurement of Deglycosylation Activity for Different Aglycone Structures and Specificity for Glycone Substrates The oxidoreductase enzyme derived from Rhizobium sp. GIN611, whose expression was induced, was reacted with the flavonoid icariin, camelliaside A or camelliaside B as a substrate in the manner described above and activity was measured by MALDI mass spectrometry. Oxidation of galactose attached to camelliaside A and deglycosylation activity thereof were identified. Also, oxidation of xylose attached to camelliaside B and deglycosylation activity thereof were identified. That is to say, the enzyme was confirmed to show deglycosylation activity for sugars attached to the flavonoid-based aglycones and to capable of degrading not only glucose but also galactose and xylose by oxidizing them (see FIGS. 12 and 13).

Example 15

Substrate Specificity for Glycone Binding

Specificity of the enzyme for α-bonding and β-bonding was investigated using 4-nitrophenyl α-D-glucopyranoside, 4-nitrophenyl β-D-glucopyranoside, 4-nitrophenyl α-D-galactopyranoside and p-nitrophenyl β-D-galactopyranoside. The enzyme showed activity for both α-bonding and β-bonding (see Table 3).

TABLE 3

| Substrates | Relative activity (%) |
|---|---|
| p-Nitrophenyl α-D-glucopyranoside | 103 |
| p-Nitrophenyl β-D-glucopyranoside | 100 |
| p-Nitrophenyl α-D-galactopyranoside | 201 |
| p-Nitrophenyl β-D-galactopyranoside | 400 |

[Accession Number]
KCTC 11708BP

---

The invention claimed is:

1. A method of deglycosylating a ginsenoside glycoside, an isoflavone glycoside or a flavonoid glycoside using a host cell transformed with a recombinant DNA vector comprising a DNA sequence encoding an oxidoreductase having the amino acid sequence of SEQ ID NO 3, or a cell extract of the host cell transformed with the recombinant DNA vector as a biocatalyst.

2. The method according to claim 1,
wherein the ginsenoside glycoside is one or more selected from a group consisting of ginsenoside compound K (CK), ginsenoside Rh2, ginsenoside F2, ginsenoside Rb1, ginsenoside Rb2, ginsenoside Rc, ginsenoside Rb3, ginsenoside F1, ginsenoside Re,
wherein the isoflavone glycoside is daidzin, or
wherein the flavonoid glycoside one or more selected from a group consisting of icariin, camelliaside A and camelliaside B.

3. The method according to claim 1,
wherein the method is for deglycosylating a sugar in the ginsenoside glycoside, the isoflavone glycoside or the flavonoid glycoside, and
the sugar is one or more selected from a group consisting of glucose, galactose, rhamnose, arabinose and xylose.

* * * * *